March 5, 1974 F. C. TOMLINSON Plant Pat. 3,501
GAZANIA PLANT
Filed Feb. 2, 1972
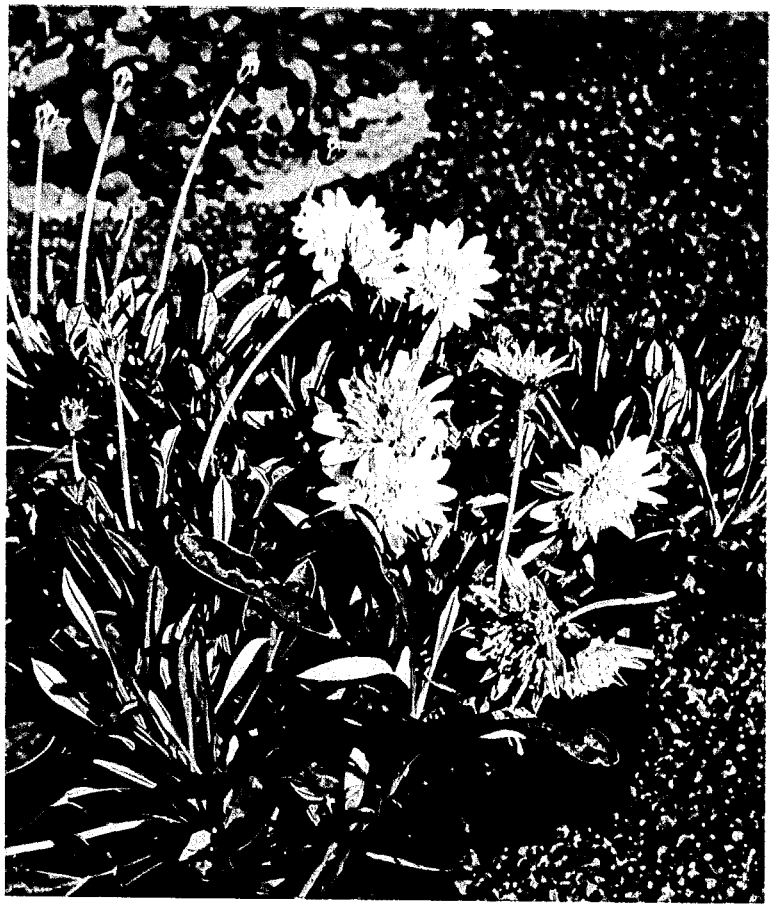

United States Patent Office

Plant Pat. 3,501
Patented Mar. 5, 1974

3,501

GAZANIA PLANT

Francis C. Tomlinson, Whittier, Calif., assignor to Select Nurseries, Incorporated, Brea, Calif.

Filed Feb. 2, 1972, Ser. No. 223,033
Int. Cl. A01h 5/00
U.S. Cl. Plt.—68 1 Claim The present invention relates to a new and distinct variety of Gazania plant.

This new and distinct variety is characterized by its extremely double type of yellow blooms that are large in diameter and are borne by the plant during the major part of the year. The flowers of the new species have an additional characteristic that distinguishes them from the flowers of other varieties of known Gazania plants which is that the flowers of the new variety remain open during the hours of darkness, whereas all other known varieties of gazanias have flowers that close up tightly at night.

The new variety was produced by me at my growing grounds that are located in Rainbow Valley, Calif., by cross breeding a chance seedling found in a bed of *Gazania splendens,* an unpatented variety, as the seed parent with a variety of Gazania identified as Royal Gold, also an unpatented variety, as the pollen parent. This cross breeding was performed by me in 1969, and the resulting plant first bloomed in 1970, when it bore the large extremely double blooms.

The new variety is distinguished from its seed parent, the chance seedling obtained from *Gazania splendens* in that said seed parent bears only single, yellow, daisy-like flowers. The new variety distinguishes from its pollen parent Royal Gold Gazania, in that the flowers of the pollen parent are of a clear gold color and are either single or semidouble blooms. The flowers of the variety are instead extremely double and are of a Lemon Yellow hue.

Asexual reproductions of the new variety have been accomplished by taking cuttings. Numerous cuttings have been made at my Rainbow Valley, Calif., location and all of the resulting plants have exhibited the above-mentioned distinguishing characteristics which have been transmited through succeeding propagations, thereby establishing that the strain is true. The plant, as far as known, does not produce seed, therefore it cannot be produced by seed.

The accompanying illustrations in full color show a number of flowers, unopened buds and groups of leaves. This colored illustration is as correct as it is possible to reproduce the color of the flowers, the medium green upper side of the leaves and the silvery gray green of the bottom side of the leaves, by this type of illustration.

A detailed description of the new variety follows; to facilitate identification of the important colors referred to in this specification, the color terminology adopted by the British Horticultural Colour Charts has been adopted.

THE PLANT

Parentage:

*Seed parent.*—Chance seedling growing in a bed of *Gazania splendens.*

*Pollen parent.*—Royal Gold variety of Gazania.

Form: Ground cover type of plant that is best described as semiupright.

Growth habit: Vigorous, spreading, and semiupright.

Foliage:

*Quantity.*—Abundant.

*Size.*—Full grown leaves are from 2½" to 3" in length and vary from 7/16" to 9/16" at the widest portion of the leaf.

*Shape.*—Leaves are oblanceolate with the apex acute. The base of the leaves is attenuate and is approximately 3/16" at the point of minimum width. This portion of the leaf base folds around the stem portion at the juncture.

*Ribs and veins.*—The veins are not prominent on the upper side and are a little more prominent on the underside of the leaf but are not sharply distinct. The central rib is very prominent on the underside of the leaf and terminates at the apex of the leaf as a sharp line.

*Texture.*—The leaves are rather thick. The upper side is waxy while the underside is densely sericeous.

*Color.*—The upper side of the leaves is Spinach Green 0960/1. The underside of the leaves is Sung Green 000658/3.

*Leaf margins.*—Entire with the majority of the leaves being semiundulate.

*Leaf arrangement.*—The leaves form in equitant groups numbering 12 to 14 leaves in each group. Several groups are usually attached to a node in a stem of large caliper. The number of groups attached to each node can vary considerably.

THE FLOWER

Blooming habit: The new variety seems to bloom throughout the year even during relatively cold portions of the year in the coastal region of Southern California.

Buds:

*Size.*—Most buds are from ½" to ⅝" in diameter, at the widest portion.

*Form.*—Buds are substantially oval shaped being pointed at the top.

*Sepals.*—Sepals on a bud about to open can be up to 35 in number. The sepals are coherent at their base end with the outer end portions becoming arcuate as they extend outwardly from the calyx. The bottom of the calyx is provided with a circular depression into which the end of the supporting stem extends to join the calyx.

*Borne.*—Flowers are borne singly on a stem that can be up to 4" in length.

*Size.*—The size of the blooms varies from 2½" to 3" in diameter. The flowers are usually larger when the weather is warm than during the colder portion of the year.

*Form.*—The overall flower is ray shaped in outline with the central petals as well as the outer petals ligulate. The central petals form a tight compact mass somewhat resembling the flower of the dandelion. The larger petals form the outer ring and number about 20; the size of the petals decreases as they approach the central portion.

*Petalage.*—Petalage is best described as ligulate with lactiferous vessels present.

*Color.*—The overall color of the flower and petals is Lemon Yellow 4.

*Petals.*—Shape: The petals have an obtuse tip that is retuse with the base of the petal cuneate. Size: The larger outer petals are approximately 1½" in length and about ½" at the widest portion.

The smaller central petals are about 1" in length and vary between 1/16" to 1/8" in width. Number: The combined number of large and small petals that form the flower is usually in excess of 500, there being approximately 525 petals in the average flower. Each petal base is surrounded by numerous exceedingly fine rachilla like filaments.

I claim:

1. A new and distinct variety of Gazania plant substantially as herein shown and described, characterized particularly as to novelty by its large extremely doubled blooms that are predominantly Lemon Yellow, by the fact that said blooms remain fully open during the hours of darkness, and by the fact that the new variety does not produce any seeds.

No references cited.

ROBERT E. BAGWILL, Primary Examiner